(12) United States Patent
Lee et al.

(10) Patent No.: US 10,349,893 B2
(45) Date of Patent: Jul. 16, 2019

(54) SMARTPHONE WITH TELEMEDICAL DEVICE

(71) Applicants: Byung Hoon Lee, Seoul (KR); Jaechun Lee, Jeju-si (KR)

(72) Inventors: Byung Hoon Lee, Seoul (KR); Jaechun Lee, Jeju-si (KR)

( * ) Notice: Subject to any disclaimer, the term of this patent is extended or adjusted under 35 U.S.C. 154(b) by 262 days.

(21) Appl. No.: 15/211,829

(22) Filed: Jul. 15, 2016

(65) Prior Publication Data
US 2017/0014079 A1 Jan. 19, 2017

(30) Foreign Application Priority Data
Jul. 16, 2015 (KR) .......................... 10-2015-0101087

(51) Int. Cl.
*A61B 5/00* (2006.01)
*A61B 5/01* (2006.01)
(Continued)

(52) U.S. Cl.
CPC .......... *A61B 5/6898* (2013.01); *A61B 5/0022* (2013.01); *A61B 5/746* (2013.01); *A61B 7/00* (2013.01); *A61B 7/003* (2013.01); *A61B 7/008* (2013.01); *A61B 7/02* (2013.01); *A61B 8/0866* (2013.01); *A61B 8/4427* (2013.01); *A61B 8/461* (2013.01); *A61B 8/54* (2013.01); *A61B 8/56* (2013.01); *G06F 19/00* (2013.01); *G16H 40/67* (2018.01); *A61B 5/0077* (2013.01); *A61B 5/01* (2013.01); *A61B 5/021* (2013.01); *A61B 5/02055* (2013.01); *A61B 5/02411* (2013.01); *A61B 5/0816* (2013.01); *A61B 5/4362* (2013.01); *A61B 5/7203* (2013.01); *A61B 5/7282* (2013.01); *A61B 8/085* (2013.01);

(Continued)

(58) Field of Classification Search
CPC ....... A61B 5/0022; A61B 5/6898; A61B 8/54; A61B 8/4416; Y02A 90/26
USPC .......................................................... 600/301
See application file for complete search history.

(56) References Cited

U.S. PATENT DOCUMENTS 5,737,429 A 4/1998 Lee
2012/0238831 A1* 9/2012 Benford ................. A61B 5/162
600/300

(Continued)

FOREIGN PATENT DOCUMENTS

KR 20-0131518 Y1 12/1998
KR 20120116331 A * 10/2012 ........... A61B 5/6829
KR 101435581 B1 * 8/2014 ............... A61B 7/04

*Primary Examiner* — Gary Jackson
*Assistant Examiner* — Zahed Kabir
(74) *Attorney, Agent, or Firm* — Knobbe Martens Olson & Bear LLP

(57) ABSTRACT

The present disclosure discloses a smartphone based telemedical devices incorporating into smartphone medical devices such as stethoscopes, thermometers, ultrasound imaging devices and/or alarm generators for diagnosis or determination of the disease or health status or condition of a user. The present smartphone based telemedical devices can be advantageously and conveniently used to measure and generate and/or remotely transmitting the medical data or information generated by the incorporated medical devices thus allowing an accurate and rapid determination of the status of a user particularly under emergency particularly when there are no regular medical or hospital services are available.

2 Claims, 24 Drawing Sheets

(51) Int. Cl.
*A61B 8/14* (2006.01)
*A61B 7/02* (2006.01)
*A61B 8/00* (2006.01)
*A61B 5/0205* (2006.01)
*A61B 7/00* (2006.01)
*A61B 8/08* (2006.01)
*G06F 19/00* (2018.01)
*G16H 40/67* (2018.01)
*A61B 5/021* (2006.01)
*A61B 5/024* (2006.01)
*A61B 5/08* (2006.01)

(52) U.S. Cl.
CPC ............... *A61B 8/14* (2013.01); *A61B 8/4416* (2013.01); *A61B 2503/06* (2013.01); *Y02A 90/26* (2018.01)

(56) References Cited

U.S. PATENT DOCUMENTS

| | | | | |
|---|---|---|---|---|
| 2012/0283583 | A1* | 11/2012 | Batkin | A61B 5/0225 |
| | | | | 600/493 |
| 2015/0087926 | A1* | 3/2015 | Raz | A61B 5/0013 |
| | | | | 600/301 |
| 2016/0106318 | A1* | 4/2016 | Rajesh | A61B 5/08 |
| | | | | 600/481 |
| 2016/0157717 | A1* | 6/2016 | Gaster | A61B 5/0444 |
| | | | | 600/301 |
| 2016/0174857 | A1* | 6/2016 | Eggers | G06F 19/3418 |
| | | | | 600/301 |
| 2016/0339300 | A1* | 11/2016 | Todasco | H04W 4/80 |

\* cited by examiner

SMARTPHONE WITH TELEMEDICAL DEVICE

CROSS-REFERENCES TO RELATED APPLICATIONS

The present application claims the benefit of Korean Patent Application No. 10-2015-0101087 filed Jul. 16, 2015 in the Korean Intellectual Property Office, disclosure of which is incorporated herein by reference in its entirety.

BACKGROUND

Field

The present disclosure is related to a smartphone equipped with a telemedical device, and more particularly, to smartphone-connected or -managed telemedical devices including stethoscopes, thermometers, blood pressure manometers and ultrasonic medical devices which may be conveniently used to diagnose a particular disease or check the status of health being connected to a smartphones by any persons including doctors.

Description of the Related Art

When a doctor examines a patient in a hospital, the doctor makes an initial diagnosis based on a medical history of the patient, a visual inspection, a palpation, percussion, auscultation using a stethoscope, and/or blood pressure. Then doctors further perform a comprehensive examination based on the initial examination results and make a precise diagnosis of a disease.

Korean Utility Model Patent No. 20-0131518 (registered on Sep. 16, 1998) and U.S. Pat. No. 5,737,429 (registered on Apr. 7, 1998) invented by the present inventor disclose a stethoscope.

SUMMARY

The present disclosure is to provide device for telemedical such as smartphone-connected or -managed telemedical devices which allows an accurate and rapid determination of the status of a patient under emergency outside of hospital environment by using such information as electrically analyzed stethoscope data, body temperature, medical images, ultrasound images, and blood pressures, which may be conveniently generated and transmitted to a doctor for diagnosis either by a patient or a general user.

One aspect of the present disclosure provides a telemedical device based on a smartphone, which may comprise a mobile application for medical examination installed and running on the smartphone; an auscultation measurement unit built into the smartphone and operated by the application; a body temperature measurement unit built into the smartphone and operated by the application; a medical image observation unit built into the smartphone and operated by the application; an alarm generator built into the smartphone and operated by the application; and a transceiver transmitting and receiving the information generated from the auscultation measurement unit, the body temperature measurement unit, the medical image observation unit and/or alarm generator to contacts predetermined through the application, wherein the auscultation measurement unit comprises a transmitting member, a noise removing member from the auscultation sound detected, a signal amplifier, a digital converter, a standard auscultation sound storing member, and a display member displaying the standard auscultation sounds compared to the standard auscultation sound, wherein the body temperature measurement unit comprises a contact or non-contact type of a temperature sensor, a body temperature storing member, and a display member displaying the temperature measured or stored, wherein the medical image observation unit comprises a camera, a observed medical image storing member and a display member displaying the medical images observed or stored, wherein the alarm generator comprises a speaker, and wherein the mobile application controls the auscultation measurement unit, the body temperature measurement unit, the medical image observation unit, the transceiver and the alarm generator, and generates an alarm in emergency and transmits the alarm and/or at least one of the information generated by the auscultation measurement unit, the body temperature measurement unit and the medical image observation unit to a predetermined contact.

A still further aspect of the disclosure provides a telemedical device based on a smartphone, which may comprise a mobile application for medical examination installed and running on the smartphone a compound medical device operated and controlled by the mobile application, the compound device including a auscultation measurement unit, a body temperature measurement unit and a medical image observation unit, and being connected to the smartphone by wire or wirelessly; an alarm generator built into the smartphone and operated by the mobile application; and a transceiver transmitting and receiving the information generated from the auscultation measurement unit, the body temperature measurement unit, the medical image observation unit and/or alarm generator to contacts predetermined through the application, wherein the auscultation measurement unit comprises a noise removing member from the auscultation sound measured, a signal amplifier, a digital converter, a standard auscultation sound storing member, and a display member displaying the standard auscultation sounds measured or recorded, wherein the body temperature measurement unit comprises a contact or non-contact temperature sensor, a body temperature storing member, and a display member display the temperature measured or recorded, wherein the medical image observation unit comprises a generated medical image storing member and a display member displaying the medical images generated, and wherein the mobile application controls the auscultation measurement unit, the body temperature measurement unit, the medical image observation unit, the transceiver and the alarm generator, and generates an alarm in emergency and transmits the alarm and/or at least one of the information generated by the auscultation measurement unit, the body temperature measurement unit and the medical image observation unit to a predetermined contact.

In the foregoing telemedical device, the mobile application further comprises a physical data input section for receiving at least one information selected from a group consisting of an age, a sex, a height, a body weight, a gestational week of pregnancy, or a mode of diagnosis, wherein the mode of diagnosis is selected from a pneumonia mode, enteritis mode, and a pregnancy mode.

In the still foregoing telemedical device, the device may further comprises an analyzing unit to compare and analyze the information generated in comparison to criteria for each of the mode of diagnosis stored in each of the storing members or a database to diagnose or determine a health status of a user, wherein the criteria for the pneumonia mode is a body temperature exceeding a predetermined range; and at least one of the lung auscultation sounds selected from rales, crackles or moist rales, or no lung auscultation sound; wherein the criteria for the enteritis mode is an auscultation metallic bowel sound or no bowel auscultation sound; and wherein the criteria for the pregnancy mode is a body temperature of a pregnant woman and an fetal heart rate measured by an auscultation.

In the still foregoing telemedical device, the criteria for the pneumonia may further comprises a pediatric pneumonia diagnosis criteria, wherein the pediatric pneumonia criteria is a respiratory rate according to the age of a user in which the respiratory rate is 60 or more per minute for a user under 2 months old, 50 or more per minute for a user between 2 to 11 months old, 40 or more per minute for a user between 11 to 59 months old.

In the still foregoing telemedical device, the mode of diagnosis is a pneumonia mode, and a user is diagnosed with a pneumonia if the user's body temperature measured by the body temperature measurement unit meets a preset criterion for diagnosis of pneumonia and the user's auscultation data measured by the auscultation measurement unit meet at least one of the preset criteria for diagnosis of pneumonia selected from a first, a second and a third criteria, wherein the first criterion is rales, crackles, or moist rales, and the second criterion is no respiratory rate detected from the pulmonary auscultation performed on the user, and wherein the criterion for the body temperature is a body temperature exceeding a predetermined range.

In the still foregoing telemedical device, the criteria for diagnosis of pneumonia further comprises a pediatric pneumonia diagnosis criterion, and a user is diagnosed having a pediatric pneumonia when the user meets the criterion, and the criterion is a respiratory rate according to the age of the user in which the respiratory rate is 60 or more per minute for a user under 2 months old, 50 or more per minute for a user between 2 to 11 months old, 40 or more per minute for a user between 11 to 59 months old.

In the still foregoing telemedical device, the mode of diagnosis is a enteritis mode, and a user is diagnosed with a enteritis if the auscultation data measured meet at least one of preset criteria for diagnosis of enteritis selected from a first and a second criteria, and the first criterion is a metallic bowel sound detected, and the second criterion is no bowel movement detected.

In the still foregoing telemedical device, the mode of diagnosis is a pregnancy mode, and a user is diagnosed as a normal pregnancy if both the auscultation data and body temperature data measured meet a preset criteria for diagnosis of pregnancy wherein the auscultation data is a range of the fetal heart rate according to the weeks of a fetus and the user is diagnosed as a normal pregnancy if the fetal heart rate is within a predetermined range according to the weeks of a fetus, wherein the body temperature data is a range or changes of the body temperature according to the weeks of pregnancy and the user is diagnosed as a normal pregnancy if the body temperature is within a predetermined range according to the weeks of pregnancy.

In the still foregoing telemedical device, the device may further comprises a blood pressure measurement unit operated by the mobile application and being connected to the smartphone by wire or wireless, and the mobile application further comprises modules for controlling the blood pressure measurement unit, storing the blood pressure and displaying the blood pressure measured, and the blood pressure measurement unit takes a form of a cuff and comprises a rubber ring for being worn on wrist or ankle and a coil spring built into the ring for providing a predetermined flexibility, a tension strength within a predetermined limit, and a reinforced endurance; a power switch, and a pressure sensor for measuring blood pressure, wherein the sensor takes a form of a tube and each end of the tube is connected to one end of the ring through a cap, one end of the coil spring is connected to the cap through a coupling unit fixed to the cap, the other end of the coil spring is connected to the power switch through a tension rod whereby the power switch is powered on by a tension strength provided the tension rod and the blood pressure is measured.

In the still foregoing telemedical device, the device may further comprise an ultrasound imaging unit operated by the mobile application and being connected to the smartphone by wire or wireless, wherein the mobile application further comprises modules for controlling the ultrasound imaging unit, storing the ultrasound image detected and displaying the image detected, wherein the ultrasound imaging unit applying the ultrasound inside of the body of a user and the detect the reflected wave of the ultrasound.

The present smartphone with telemedical devices can be advantageously used for conveniently determining or checking the health status of a user by anyone through a mobile application based on heath data such as a body temperature, stethoscopes sound and medical images. Also such information may also be transmitted to a doctor for a comprehensive diagnosis and/or alarms are generated under emergency which is then transmitted to predetermined contact allowing the rapid and efficient handling of emergency.

It is a further advantage of some of the above aspects of the invention that by integrating the chambers used for the reaction and the detection of the reaction products in one device. In a typical chromatographic method, the reaction process and the detection of the reaction products are performed in separate devices resulting the cross-contamination between reagents and/or inaccurate amount of sample loading can be avoided.

BRIEF DESCRIPTION OF THE DRAWINGS

FIG. 1A is a front view of a smartphone in which various mobile applications are installed.

FIG. 1B is a rear view of FIG. 1A.

FIG. 1C is a side view of FIG. 1A.

FIG. 1D is a block diagram of a control module of a smartphone operated by a mobile application.

FIG. 2A is a front view of a smartphone in which various mobile applications are installed.

FIG. 2B is a perspective view of a compound examination device with wire and/or wireless connectivity to a smartphone as shown in FIG. 2A.

FIG. 2C is a block diagram of a control module of the compound examination device operated by a mobile application.

FIG. 3A IS a front view of a smartphone in which various mobile applications are installed.

FIG. 3B is a rear view of FIG. 3A.

FIG. 3C is a side view of FIG. 3A.

FIG. 3D is a block diagram of a control module of a smartphone operated by a mobile application.

FIG. 3E is a perspective view of a blood pressure measurement unit which can be connected to a smartphone wirelessly.

FIG. 3F is a block diagram of a control module of a blood pressure measurement unit operated by a mobile application.

FIG. 4A is a front view of a smartphone in which various mobile applications are installed.

FIG. 4B is a perspective view of a compound examination device with wire and/or wireless connectivity to a smartphone as shown in FIG. 4A.

FIG. 4C a block diagram of a control module of a compound examination device operated by a mobile application.

FIG. 4D is a perspective view of a blood pressure measurement unit which can be connected to a smartphone wirelessly.

FIG. 4E is a block diagram of a control module of a blood pressure measurement unit operated by a mobile application.

FIG. 5A is a front view of a smartphone in which various mobile applications are installed.

FIG. 5B is a perspective view of a compound examination device equipped an ultrasound imaging unit with wire and/or wireless connectivity to a smartphone as shown in FIG. 5A.

FIG. 5C a block diagram of a control module of a compound examination device equipped with ultrasound imaging unit operated by a mobile application.

FIG. 5D is a block diagram of a control module of ultrasound imaging unit operated by a mobile application.

FIG. 5E is a perspective view of a blood pressure measurement unit which can be connected to a smartphone wirelessly.

FIG. 5F is a block diagram of a control module of a blood pressure measurement unit operated by a mobile application.

DETAILED DESCRIPTION OF EMBODIMENTS

Figure 1A:
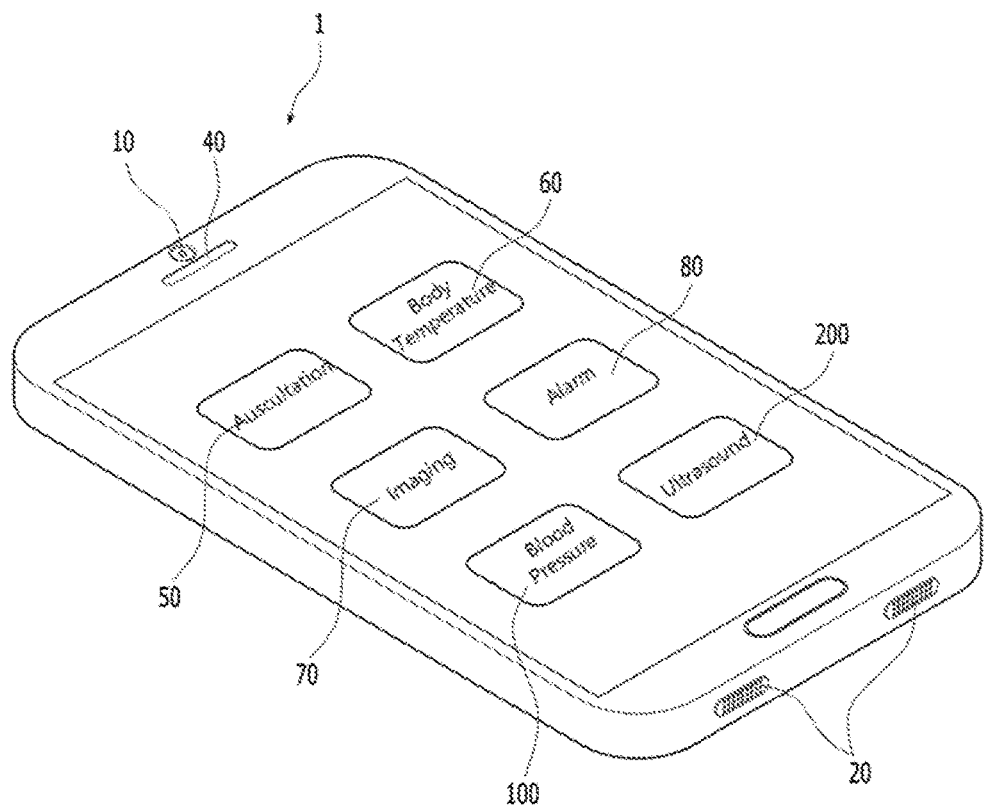
FIGS. 1A to 1D are diagrams showing various aspect of a smartphone equipped with a telemedical device, according to an embodiment of the present invention.

Various embodiments will be described with reference to the accompanying drawings. Like reference numerals in the drawings denote like elements. Various descriptions are provided to facilitate understanding of the present invention.

However, it is evident that such embodiments may be implemented without detailed description. In other examples, well-known structures and apparatuses are provided in block diagrams for convenient description of the embodiments.

In the present specification, the terms "component," "module," and "system" refer to computer-related entity, hardware, firmware, and software, a combination of software and hardware, or execution of software. For example, a component may be, but is not limited to, processes executed in a processor, a processor, an object, an execution thread, a program, and/or a computer. For example, an application executed in a computing device and a computing device may both be components. One or more components may be included in a processor and/or an execution thread, and a component may be localized in one computer, or distributed among two or more computers. Also, such components may be executed from various computer-readable media that include various data structures. For example, the components may communicate via local and/or remote processing according to signals (e.g., data from a component that interacts with another component in a local system or a distribution system, and/or data from another system and a network such as the Internet transmitted through signals) with at least one data packet.

The descriptions of the embodiments are provided such that one of ordinary skill in the art to which the present invention pertains may use or implement the present invention. Various modifications of the embodiments will be evident to one of ordinary skill in the art to which the present invention pertains. General principles defined herein may be applied to other embodiments without departing from the scope of the present invention.

Therefore, the present invention is not limited to the embodiments provided herein, but should be interpreted in a broad sense that is consistent with the principles and novel features described herein.

The term "mobile platforms" as used herein refers to a computing platform, with or without wireless connectivity, which are handheld in nature. Examples of the mobile platforms include mobile computers such as smartphones, tablet computers, or other portable computers. In one embodiment, smartphones are used. The term "smartphones" refers to a handheld device that integrates mobile phone capabilities and the features of a handheld computer or PDA. Smartphones allow users to use it as a computer to store information, e-mail, or install programs via external or internal keyboard, VGA or HDMI terminals along with using a mobile phone in one device. The smartphones allow a wireless connection to internet or intranet. Also variety of mobile applications (mobile apps) commercial or tailored to particular functions can be executed or run on a mobile platform.

When performing auscultation by listening to auscultation sounds with a stethoscope and diagnosing based on the sounds, doctors may uses electronic stethoscopes where the diagnose is made based on an electrically analyzed auscultation sounds detected via a stethoscope instead of a auscultation sound directly heard by doctors. In electronic stethoscopes, a processor electrically analyzes types of auscultation sounds that vary according to auscultated part of the body so that a more objective auscultation result is obtained. Further such electronic stethoscopes are more amenable to a telemedical device since the data are provided as digital information. For example, using a portable mobile phone-stethoscope invented by the present inventor, a telemedical is made possible by transmitting auscultation information/signals to a mobile phone at a remote site for diagnosis.

Medical devices which are amenable to digitization include thermometers, blood pressure manometers, auriscopes for visual examination of the ear and throat, ultrasonic medical devices and alarm generators. Such medical devices allow telemedical at a place such as home without visiting the clinics. Thus, doctors may be able to diagnose a disease and prescribe a medicine accordingly. However, typical medical devices used for telemedical have complex structures and the high cost for universal or common use deterring the commercialization thereof.

Figure 1B:
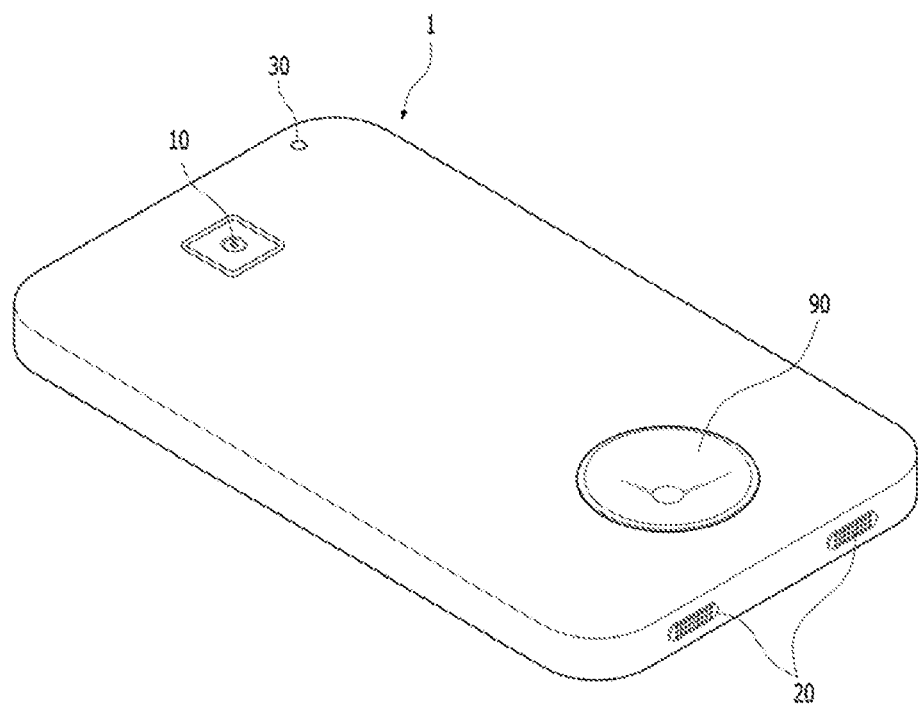
Figure 1C:
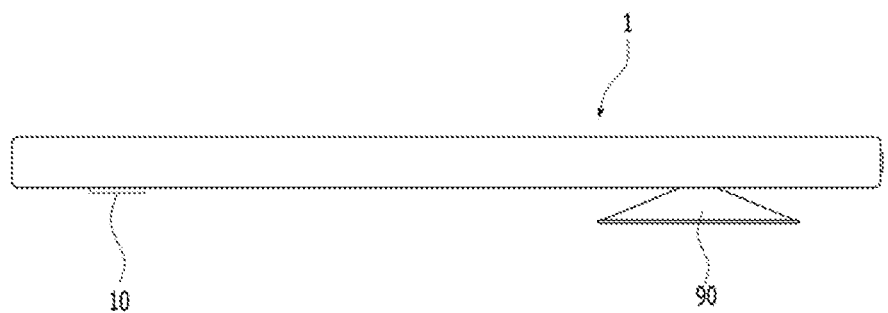
Figure 1D:
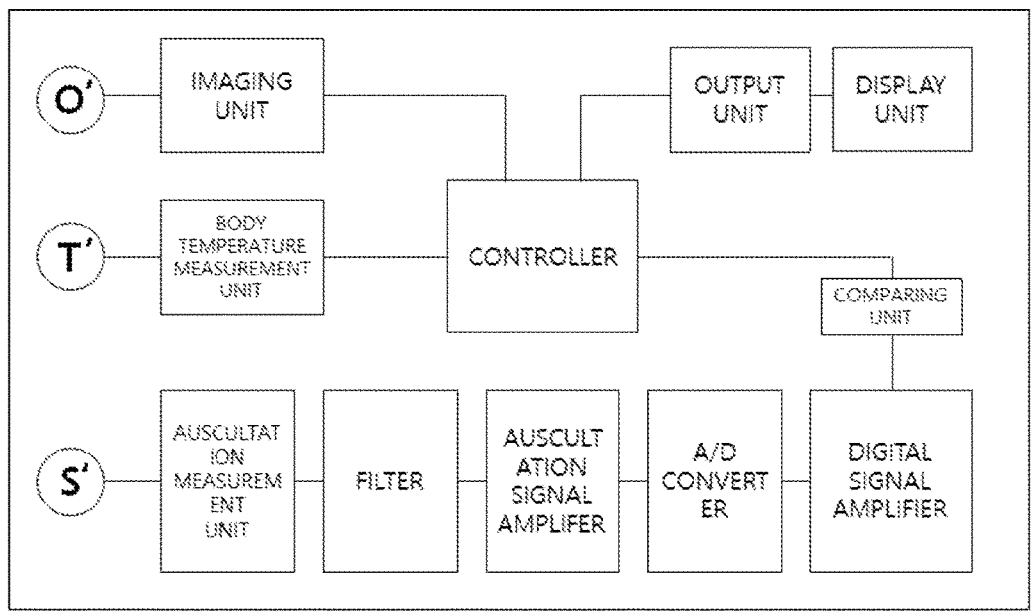

FIGS. 1A to 1D are diagrams showing various aspect of a smartphone with an integrated compound telemedical device, according to an embodiment of the present invention. FIG. 1A is a front view of a smartphone in which various mobile applications are installed. FIG. 1B is a rear view of FIG. 1A. FIG. 1C is a side view of FIG. 1A. FIG.

1D is a block diagram of a control module of a smartphone operated by a mobile application. In one embodiment, the compound device integrated with the smartphone includes a stethoscope sound measurement unit, a body temperature measurement unit and a medical image observation unit.

According to one embodiment, the smartphone, particularly smartphones with telemedical capabilities include a mobile app for medical examination installed in the smartphone (1); a stethoscope sound measurement unit (90) with a temperature sensor which is controlled by the mobile app and positioned or mounted on the backside of the smartphone; a body temperature measurement unit (30) taking body temperature using laser beam which is controlled by the mobile app; a medical image observation unit (10) integrated with the smartphone which is controlled by the mobile app; an alarm generating unit (40) integrated with the smartphone which is controlled by the mobile app; and a transmitter-receiver or transceiver unit which transmits and receives the information generated from the stethoscope sound measurement unit, the body temperature measurement unit, the medical image observation unit and/or the alarm generator to the contacts predetermined through the application.

According to one embodiment of the present disclosure, the stethoscope sound measurement unit or part includes a transmitting member (20), a noise removing member, a signal amplifier, a digital converter, a standard stethoscope sound storing member and a display member for displaying the standard stethoscope sound. The body temperature measurement unit (30) includes a non-contact type temperature sensor; a body temperature storing member; and a display member for displaying the body temperature. The medical image observation unit (10) includes a smartphone camera member; a measured image storing member; and a display member. The alarm generating unit (40) includes a smartphone speaker. The mobile application controls the stethoscope sound measurement unit running app (50), the body temperature measurement unit running app (60), the medical image observation unit running app (70), the alarm generator running app (80) and transceiver unit by using an internal smartphone control module. In one embodiment, the stethoscope sound measurement unit (90) is equipped with a contact type temperature sensor. The body temperature measurement unit (30) is equipped with a non-contact type temperature sensor using a laser beam.

According to one embodiment of the present disclosure, the smartphone, particularly smartphones with telemedical capabilities of the present disclosure can be used to determine the health status (name of disease, pregnancy and the like) of the user based on the information measured and collected by the present device. Also the present device may transmit such information to a server which is accessible by a smartphone and the health status of the user may be determined by the server.

The internal control module of the present smartphone based telemedical device includes a auscultation mode designation member (S'); a detection member connected to a auscultation microphone; a filtering member filtering only the auscultation sound and removing noises such as sounds from the body other than auscultation sound and any background sound other than from the body; a auscultation sound amplifier to amplify the filtered auscultation sound; an A/D converter to convert the amplified analog wave signal to a digital signal; a signal amplifier to amplifying the converted digital signal; a body temperature mode designation member (T') designating a body temperature measurement mode; a body temperature measurement member; a medical image observation mode designation member designating a medical image observation mode; a medical image observation mode, an analysis member including a database of a standard information on various disease in which the auscultation sounds are provided according to each type/kind of disease in reference to body temperatures, and searching and comparing the database with the obtained information; a central controlling member to determine or read out the name of disease and control each member; a output member to output the readouts; and a display member for visual representation of the readout in the smartphone. This information generated by the present device may be transmitted to a doctor along with the medical image data generated.

Figure 2A:
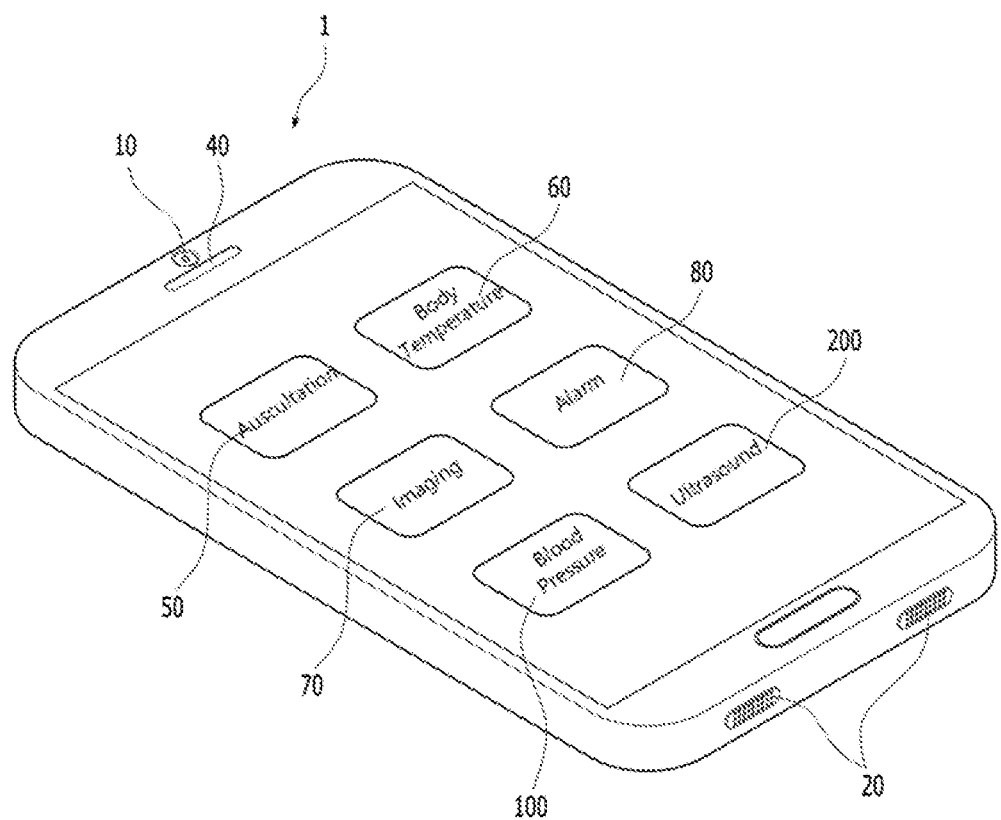
FIGS. 2A to 2C are diagrams showing various aspect of a smartphone equipped with a detachable telemedical device according to another embodiment of the present invention.
Figure 2B:
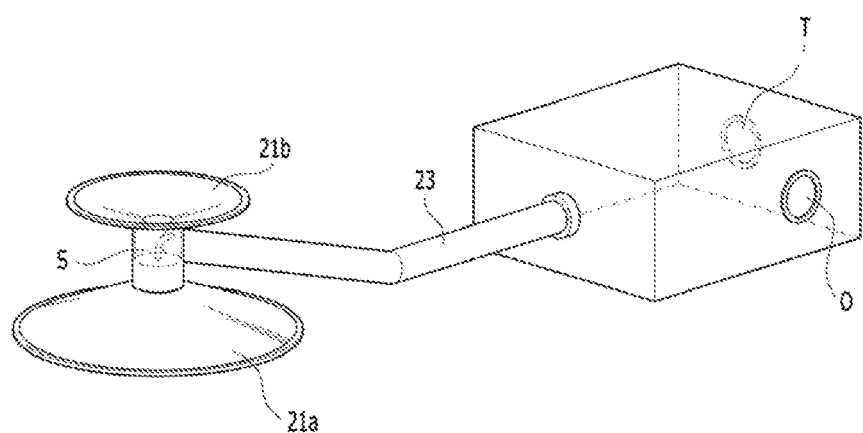
Figure 2C:
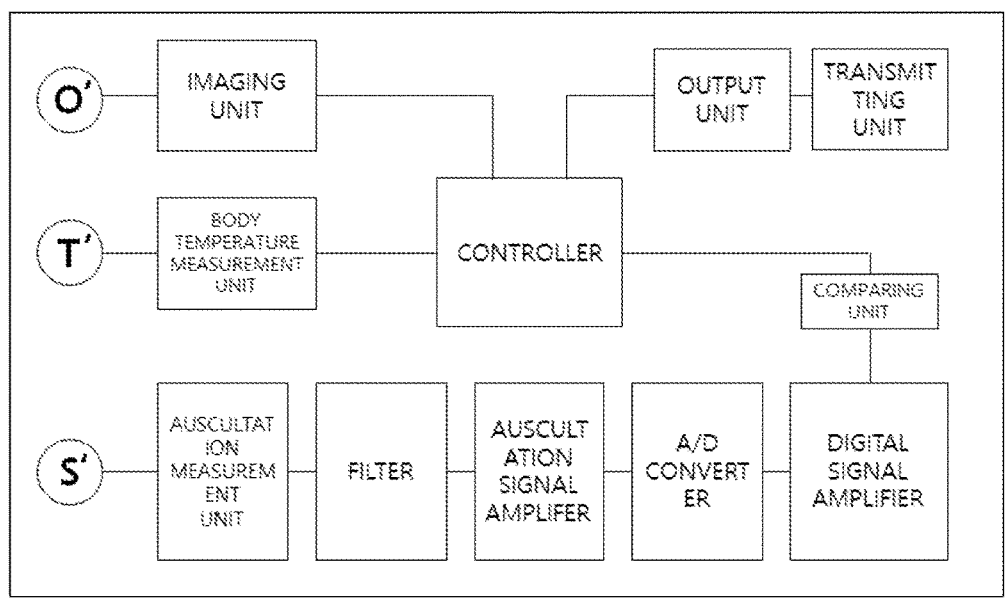

FIGS. 2A to 2C are diagrams showing various aspect of a smartphone equipped with a detachable telemedical device according to another embodiment of the present invention. FIG. 2A is a front view of a smartphone in which various mobile applications are installed. FIG. 2B is a perspective view of a compound examination device which can be connected by wire or wireless to a smartphone as shown in FIG. 2A. FIG. 2C is a block diagram of a control module of the compound examination device operated by a mobile application.

According to other embodiment of the present disclosure, the smartphone, particularly smartphones with telemedical capabilities of the present disclosure includes a mobile application for medical examination installed in the smartphone; a compound medical device, with wire or wireless connection to the smartphone, controlled or run on by the application; an alarm generating member integrated with the smartphone controlled or run on by the application; a transceiver unit which transmits and receives the information generated from the auscultation sound measurement unit, the body temperature measurement unit, the medical image observation unit and/or the alarm generator to the contacts predetermined through the application.

According to other embodiment of the present disclosure, the compound medical device included in the present smartphone based telemedical device includes an auscultation sound measurement member (S), a body temperature measurement member (T), and a medical image observation member (O). The auscultation sound measurement member is equipped with a sound collector for adults (21a) or for children (21b), the diameter of which is about 4 cm and 2.5 cm, respectively. In one embodiment of the present disclosure, the auscultation sound collector includes a supporting tube (23), a noise removing member, a signal amplifier, a digital converter, an auscultation sound storing member and a displaying member to display results from comparison with the standard information. The body temperature measurement member includes a storing member storing the body temperature measured and a display. The medical image observation member includes a medical image storing member and a display. The mobile application controls the auscultation sound measurement member, the body temperature measurement member, and the medical image observation member and the alarm generator and the transceiver using a control module installed in the smartphone or in the compound device.

The internal control module installed in the compound medical device includes an auscultation mode designation member (S'); a detection member connected to a auscultation microphone; a filtering member filtering only the auscultation sound and removing other bodily sounds and any background sound not originating from the body; an auscultation sound amplifier to amplify the filtered auscultation sound; an A/D converter to convert the amplified analog wave signal to a digital signal; a signal amplifier to amplifying the converted digital signal; a body temperature mode designation member (T') designating a body temperature measurement mode; a body temperature measurement member; a medical image observation mode designation member (0') designating a medical image observation mode; a medical image observation mode, an analysis member including a database of a standard information on various disease in which the auscultation sounds are provided according to each type/kind of disease in reference to body temperatures, and searching and comparing the database with the obtained information; a central controlling member to determine or read out the type of kind of disease and control each member; a output member to output the readouts; and a transmitting member for sending the readouts along with the medical image to the smartphone.

According to one embodiment of the present disclosure, the mobile application installed in the smartphone integrated with an auscultation unit controls the control module and the power. The related information is displayed on the smartphone so that when the application is started, a power switch, a watching switch and a remote transmit-receive switch are displayed. The display panel is configured as a touch screen. When the liquid display window is a touch screen, a user may input at least one information such as age, sex, height, body weight, gestational weeks of pregnancy, and diagnosis mode through the touch screen.

According to one embodiment of the present disclosure, the diagnosis mode is a pneumonia mode, an enteritis mode, and a pregnancy mode but the modes are not limited thereto. The touch screening including a touch panel may function as a member for inputting the user information.

The display screen for the mobile application may include a mode selection member for selecting which auscultation mode a user desires, i.e., auscultation mode for heart, lung, or enteritis, or a mode for checking health status of a pregnant woman. The mode selection member may be integrated with the user information input member.

According to one embodiment of the present disclosure, for the auscultation sound measurement unit, a transmitting unit for audio communication of the smartphone may be used. The body temperature measurement unit may be a temperature sensor mounted on the part of a smartphone a user generally touches. In one embodiment, the temperature sensor is an element the resistance of which changes by contact so that the body temperature of a user is electrically detected according to the changes in the current of the sensor or the changes in the voltage of the sensor. As described above, the temperature sensor may be configured as a contact type. Or, the temperature sensor may be configured as a non-contact type. When the sensor is a non-contact type, the sensor may be positioned in various parts of a smartphone.

Also, for the integrated medical image observation unit in the smartphone, a smartphone camera may be used. In one embodiment, the auriscopic medical image observation unit may be mounted on the smartphone as a hinge type and may also be served as a non-contact type temperature sensor and/or auscultation unit.

According to one embodiment of the present disclosure, the auscultation sound measurement unit, the body temperature measurement unit, and the medical image observation unit, which are connected to the smartphone by wire or wirelessly may use the power supply of the smartphone, or may be provided with a separate power supply. The auscultation sound measurement unit, the body temperature measurement unit, and the medical image observation unit, which are connected to the smartphone by wire or wirelessly may be operated under the control by the mobile application in connection with the smartphone. The auscultation sound measurement unit, the body temperature measurement unit, and the medical image observation unit, which are connected to the smartphone by wire or wirelessly may be configured as all-in-one type structure. In embodiments, a sound waver sensor detecting the auscultation sound, a temperature sensor measuring body temperature by contact or non-contact type, and a light source for medical examination and an imaging element may be integrated to form all-in-one type structure. The light sources which may be included are LED and LD and the like and the imaging element which may be included are CCD and CMOS and the like.

The present mobile application includes apps to control an auscultation mode designation member; an auscultation sound detection member; a filtering member filtering only the designated auscultation sound and removing other bodily sounds and any background sounds not originating from the body; an auscultation sound amplifier to amplify the filtered auscultation sound; an A/D converter to convert the amplified analog wave signal to a digital signal; a signal amplifier to amplifying the converted digital signal. The auscultation sounds may include blood flow sounds, breathing sounds, and gastro-intestinal movement sounds. When the auscultation sounds include blood flow sounds, breathing sounds, and gastro-intestinal movement sounds, an algorithm for analyzing each of the auscultation sounds may be employed.

Figure 3A:
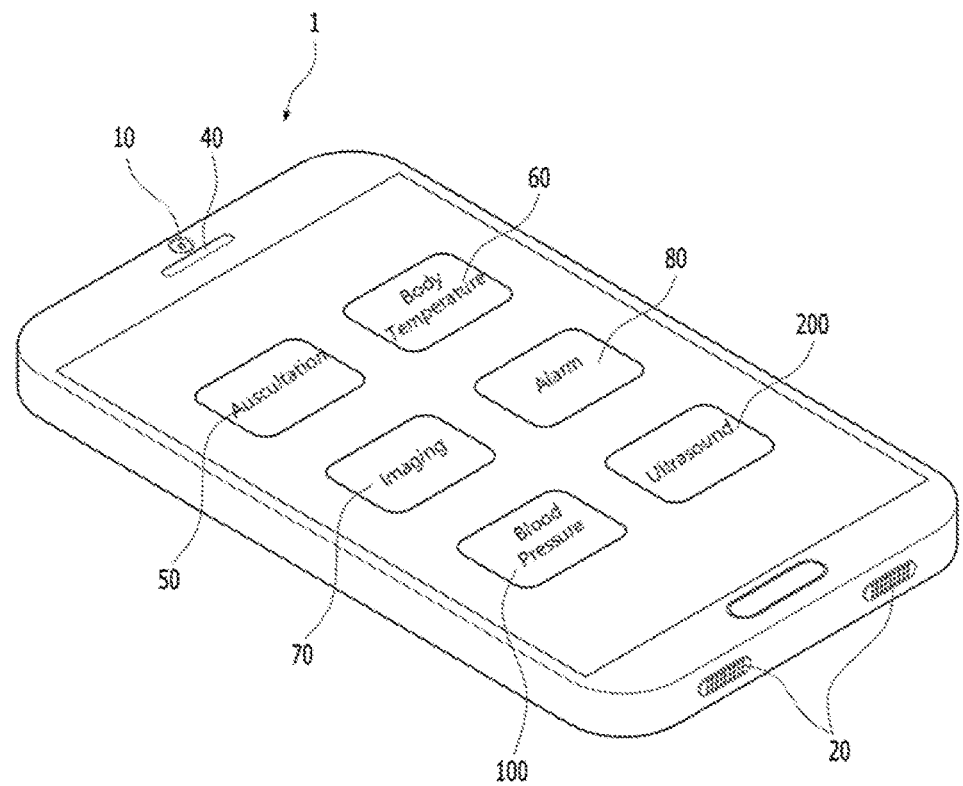
FIGS. 3A to 3F are diagrams showing various aspect of a smartphone equipped with a blood pressure measurement unit in addition to an embedded compound device.
Figure 3B:
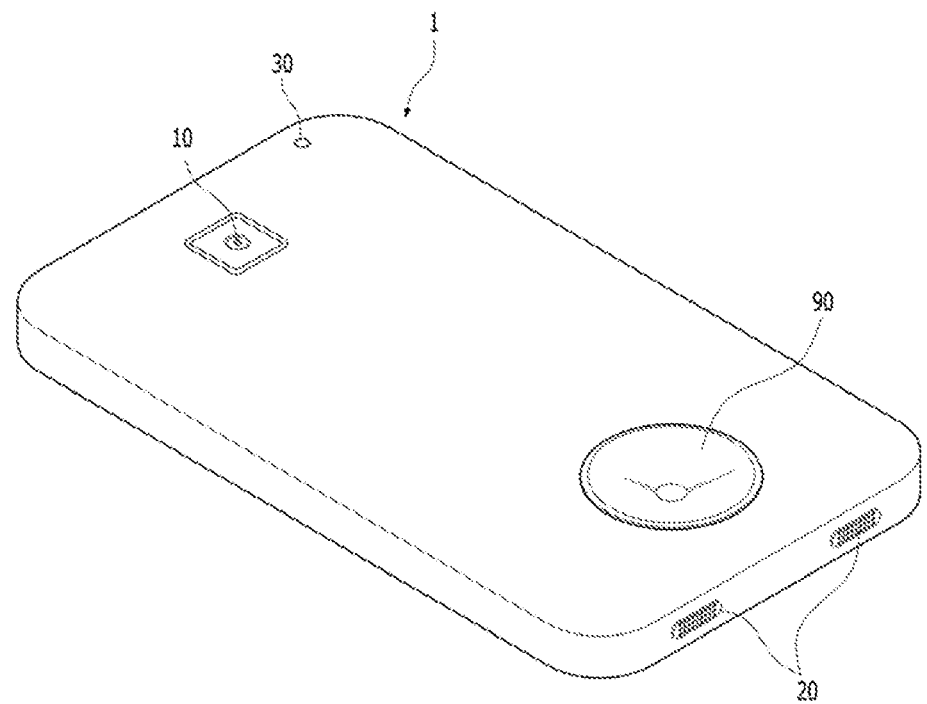
Figure 3C:
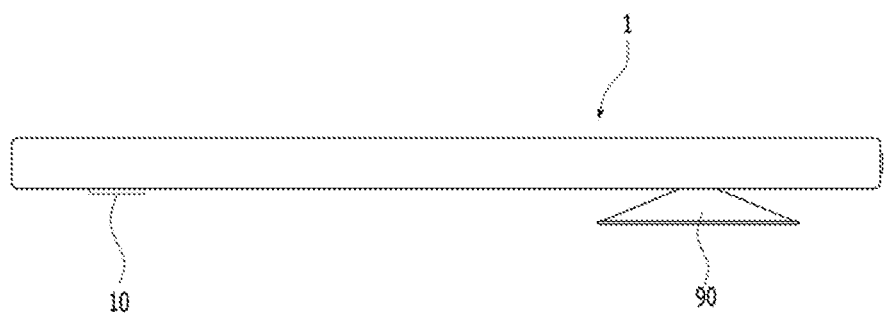
Figure 3D:
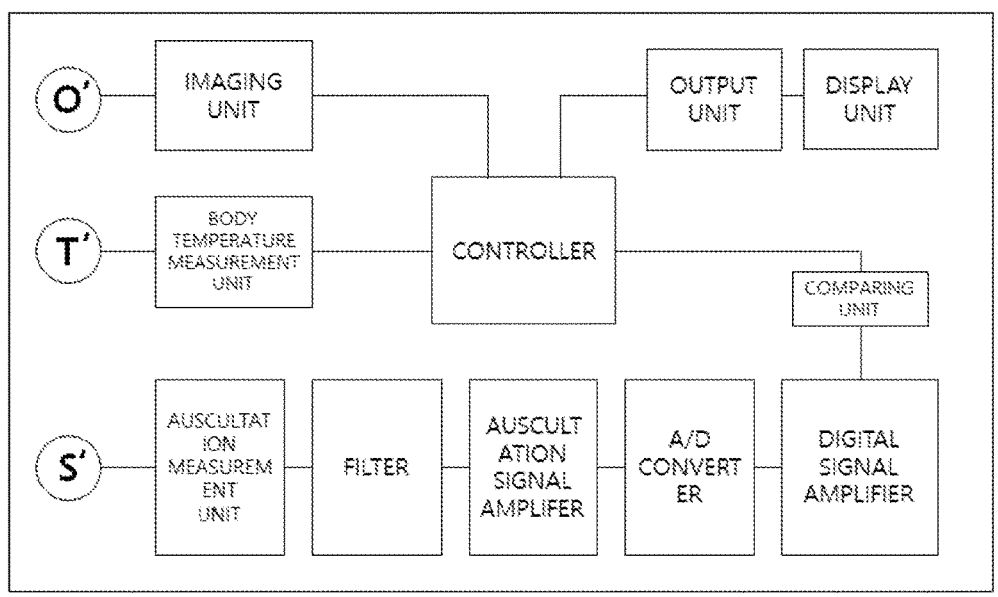
Figure 3E:
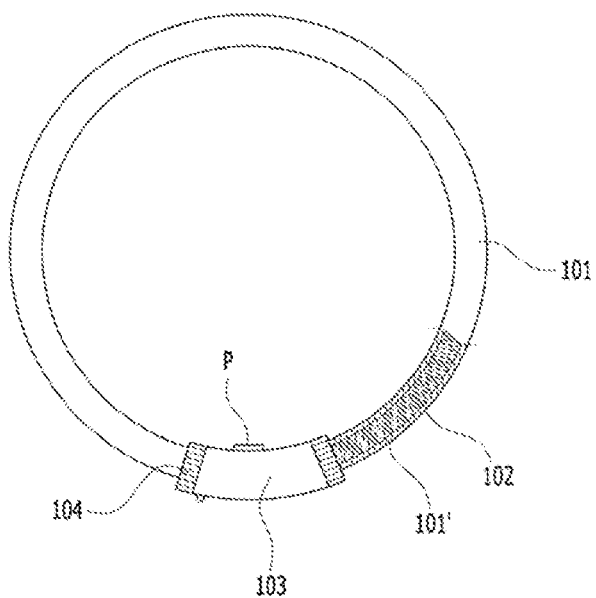
Figure 3F:
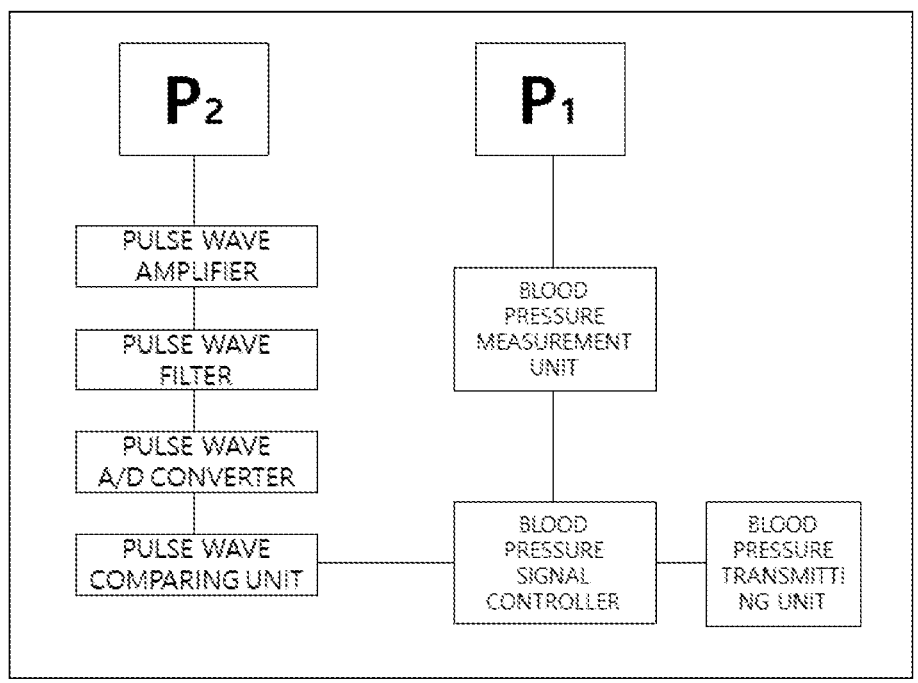

FIGS. 3A to 3E are diagrams showing various aspect of a smartphone equipped with a blood pressure measurement unit in addition to an embedded compound device. FIG. 3A IS a front view of a smartphone in which various mobile applications are installed. FIG. 3B is a rear view of FIG. 3A. FIG. 3C is a side view of FIG. 3A. FIG. 3D is a block diagram of a control module of a smartphone operated by a mobile application. FIG. 3E is a perspective view of a blood pressure measurement unit which can be connected to a smartphone wirelessly. FIG. 3F is a block diagram of a control module of a blood pressure measurement unit operated by a mobile application. In one embodiment, the present smartphone based telemedical device further comprises a blood pressure measurement unit which is wirelessly connected to the smartphone and controlled by an application. The application for running the blood pressure unit is configured to have a control function for controlling the blood pressure unit, a storing function for blood pressure measured and a display function. The blood pressure measurement unit may have a form of a cuff and includes a circular rubber ring wearable on the wrist or the ankle (101); a coil spring built into the ring for providing a predetermined flexibility, a tension strength within a predetermined limit, and a reinforced endurance; a controller (103) fixed to the rubber ring through a cap (104); and a pressure sensor (P) for measuring blood pressure.

The control module for controlling the blood pressure measurement unit includes a blood pressure mode designation member (P1) designating hemadynamometry mode, a blood pressure measurement member, a pulse wave designation member (P2) designating pulse measurement, a pulse measurement member, a pulse wave amplifier amplifying the wave data of the pulse sound measured by the pulse measurement member, a pulse wave filtering member filtering the noise, a A/D converter converting the analog signal of the pulse wave to a digital signal, a analyzing member to determine the type of the pulse wave measured by analyzing the form of the pulse wave measured, a blood pressure signal controlling member to figure out the blood pressure in reference to the pulse wave measured and a transmitting member to transmit the blood pressure signal to a smartphone and the like.

Figure 4A:
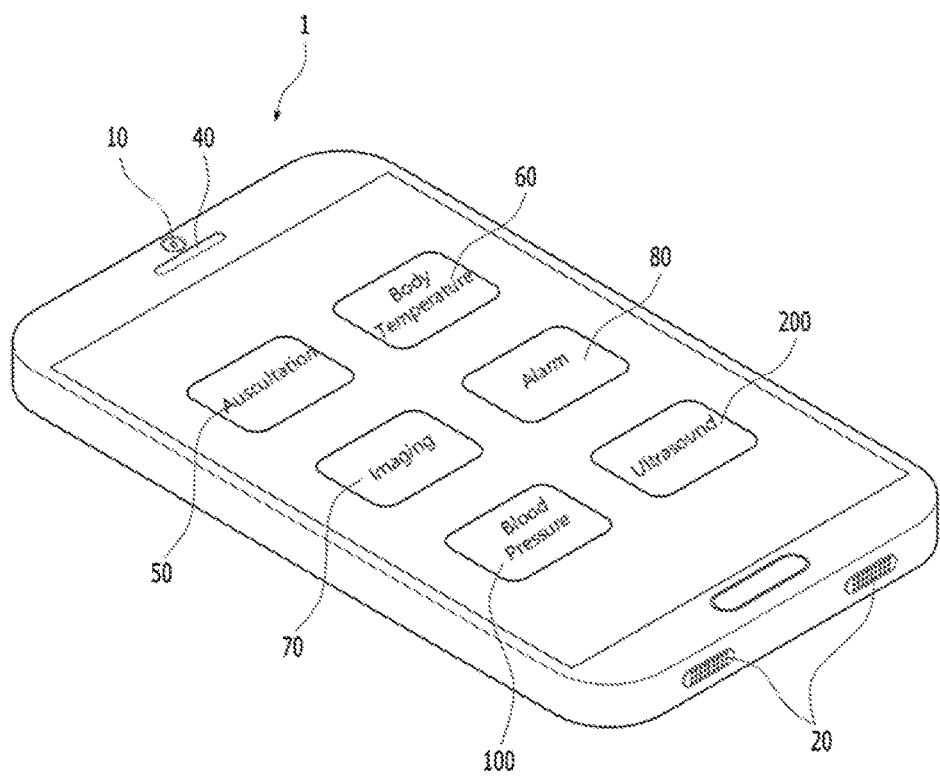
FIGS. 4A to 4E are diagrams showing various aspect of a smartphone equipped with a blood pressure measurement unit and detachable compound device according to an embodiment of the present invention.
Figure 4B:
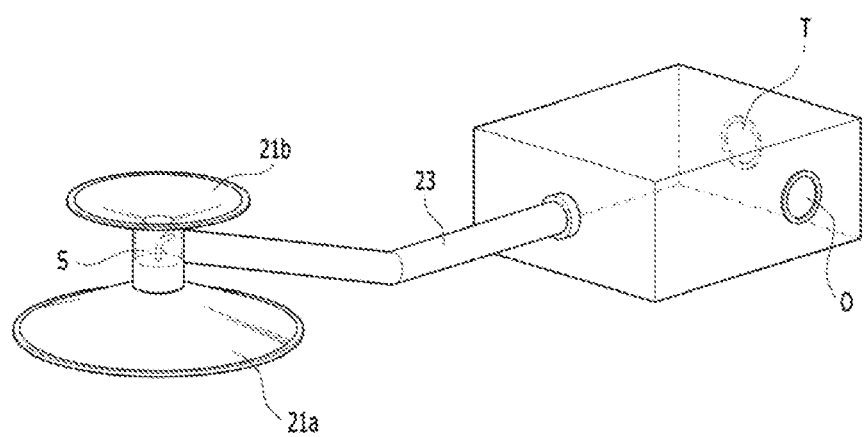
Figure 4C:
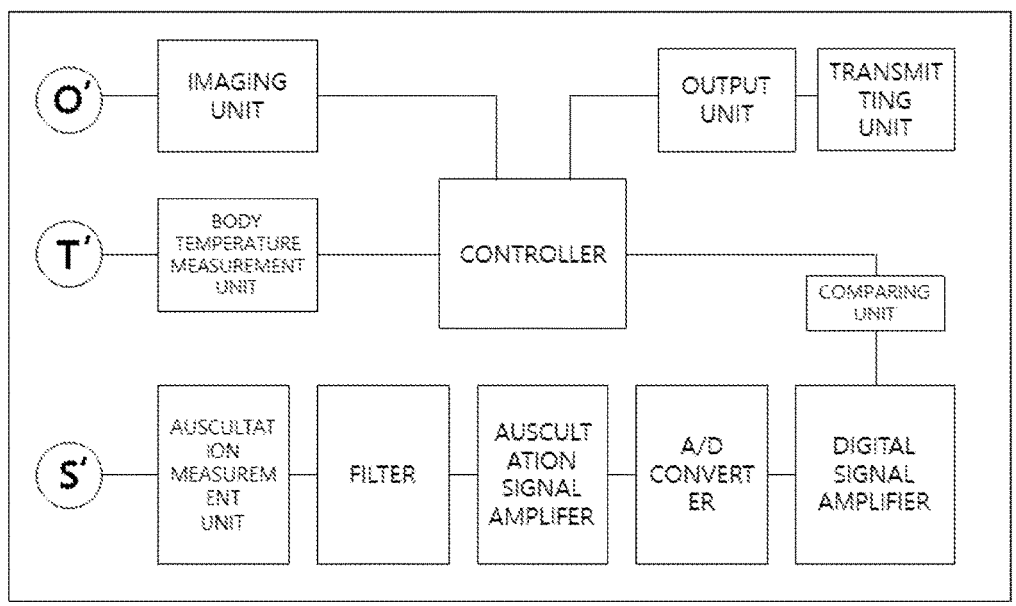
Figure 4D:
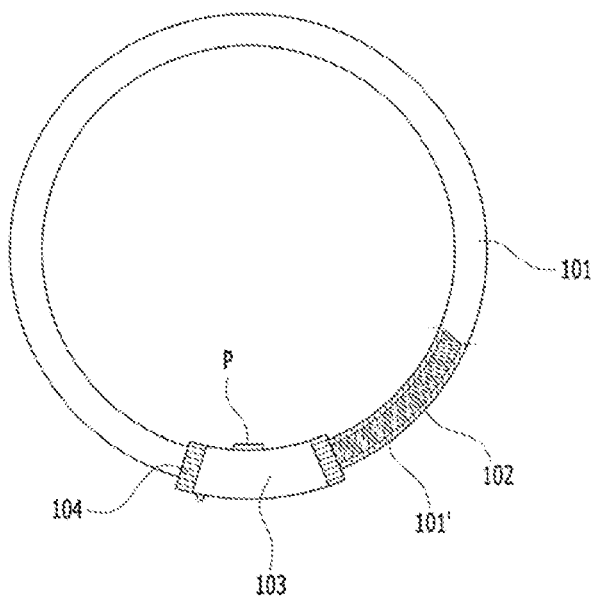
Figure 4E:
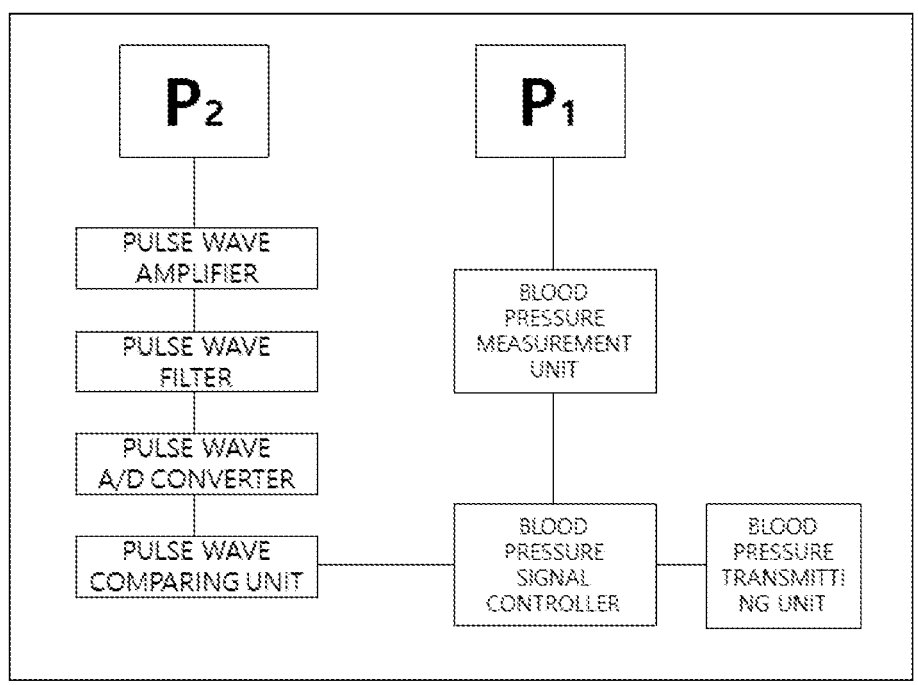

FIGS. 4A to 4E are diagrams showing various aspect of a smartphone equipped with a blood pressure measurement unit and detachable compound device according to an embodiment of the present invention. FIG. 4A is a front view of a smartphone in which various mobile applications are installed. FIG. 4B is a perspective view of a compound examination device which can be connected by wire or wireless to a smartphone as shown in FIG. 4A. FIG. 4C a block diagram of a control module of a compound examination device operated by a mobile application. FIG. 4D is a perspective view of a blood pressure measurement unit which can be connected to a smartphone wirelessly. FIG. 4E is a block diagram of a control module of a blood pressure measurement unit operated by a mobile application.

According to one embodiment of the present disclosure, the present smartphone based telemedical device further comprises a blood pressure measurement unit which is operated by a mobile application and wirelessly connected to the device. The mobile application includes a function for controlling the blood pressure unit, a function for storing the measured blood pressure and a display function. The blood pressure measurement unit may have a form of a cuff and includes a circular rubber ring wearable on the wrist or the ankle; a coil spring built into the ring for providing a predetermined flexibility, a tension strength within a predetermined limit, and a reinforced endurance; a power switch; and a pressure sensor for measuring blood pressure. The sensor takes a form of a tube and each end of the tube is connected to one end of the ring through a cap, one end of the coil spring is connected to the cap through a coupling member fixed to the cap, the other end of the coil spring is connected to the power switch through a tension rod whereby the power switch is powered on by a tension strength provided by the tension rod so that the blood pressure is measured.

Figure 5A:
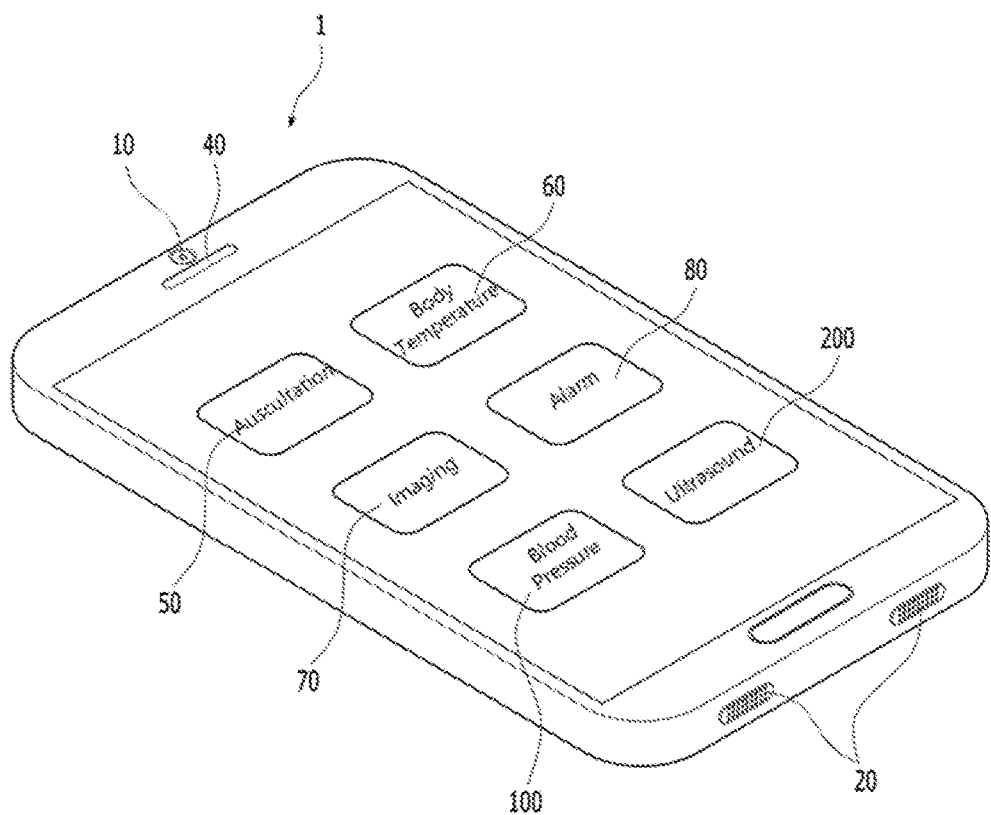
FIGS. 5A to 5F are diagrams showing various aspect of a smartphone equipped with a body temperature measurement unit and ultrasound imaging unit as well as detachable compound device according to an embodiment of the present invention.
Figure 5B:
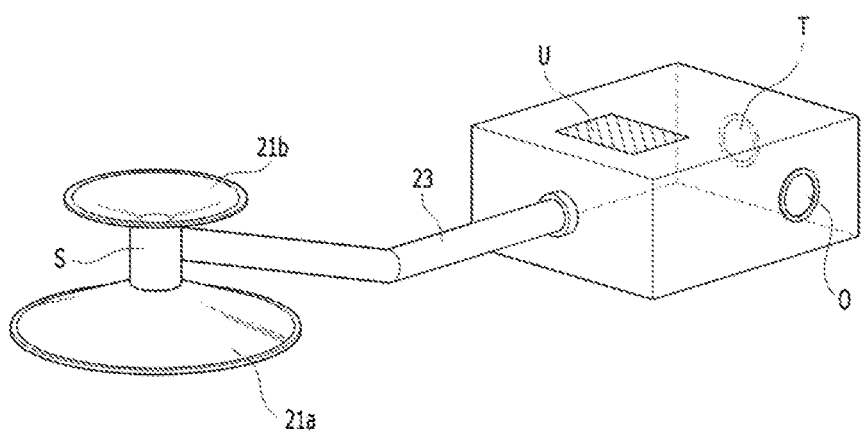
Figure 5C:
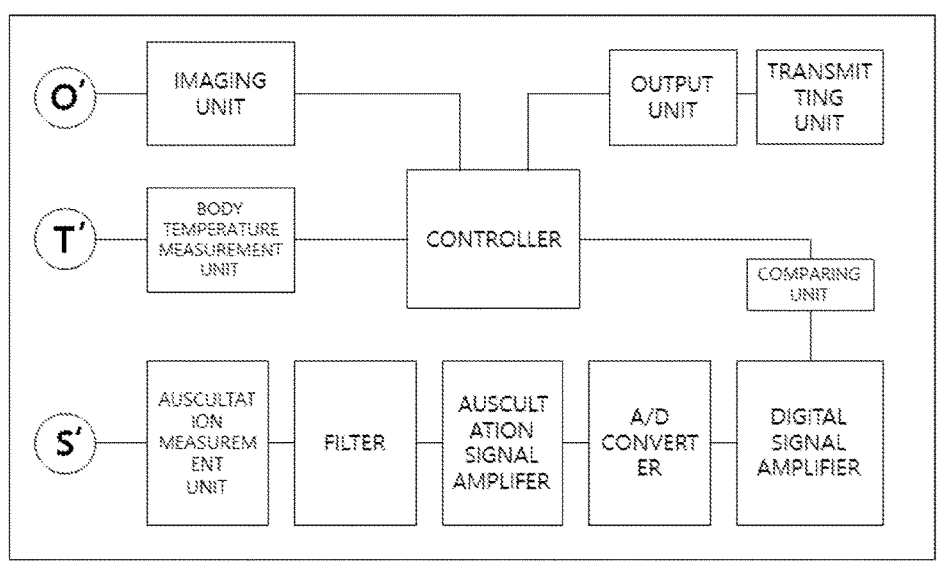
Figure 5D:
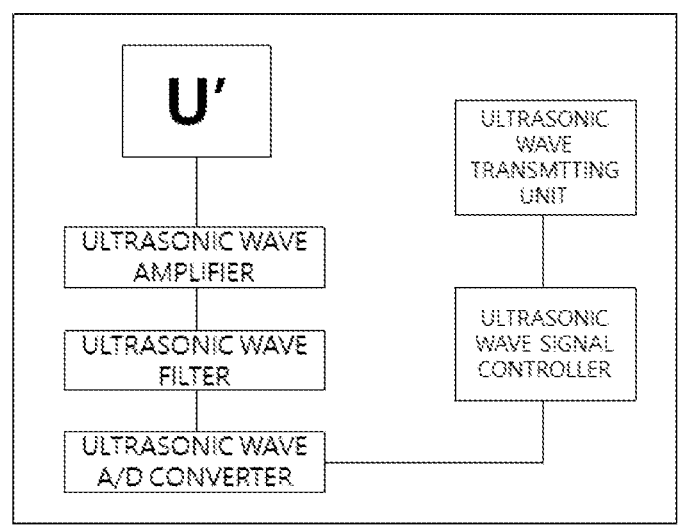
Figure 5E:
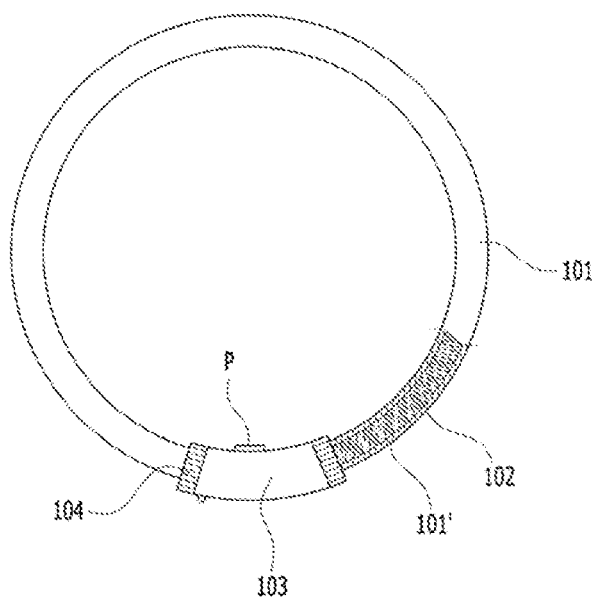
Figure 5F:
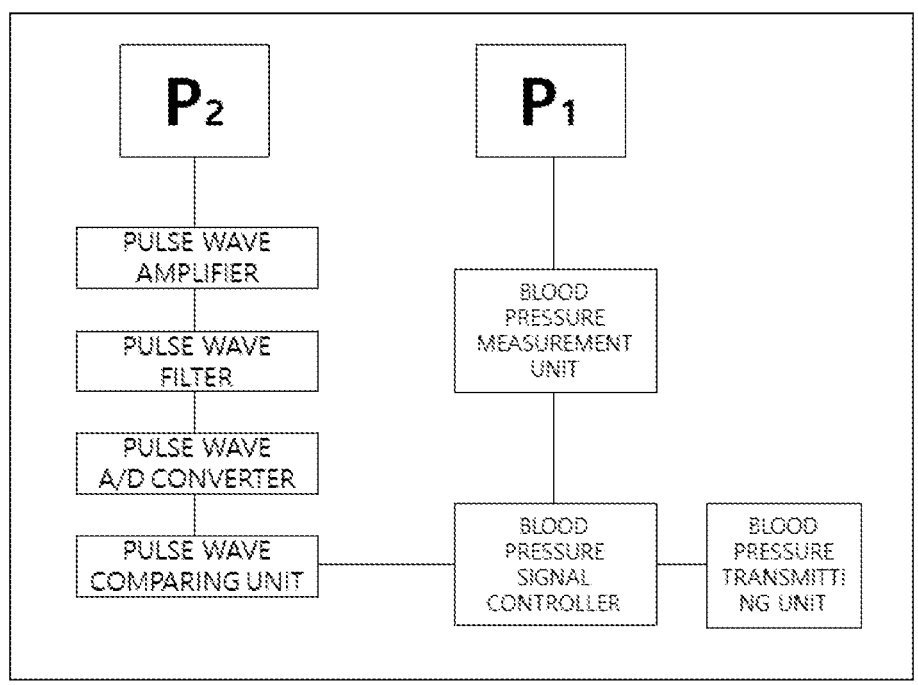

FIGS. 5A to 5F are diagrams showing various aspect of a smartphone equipped with a body temperature measurement unit and ultrasound imaging unit as well as detachable compound device according to an embodiment of the present invention. FIG. 5A is a front view of a smartphone in which various mobile applications are installed. FIG. 5B is a perspective view of a compound examination device equipped an ultrasound imaging unit which can be connected by wire or wireless to a smartphone as shown in FIG. 5A. FIG. 5C a block diagram of a control module of a compound examination device equipped with ultrasound imaging unit operated by a mobile application. FIG. 5D is a block diagram of a control module of ultrasound imaging unit operated by a mobile application. FIG. 5E is a perspective view of a blood pressure measurement unit which can be connected to a smartphone wirelessly. FIG. 5F is a block diagram of a control module of a blood pressure measurement unit operated by a mobile application.

According to one embodiment of the present disclosure, the present smartphone based telemedical device further comprises an ultrasound imaging unit which is operated by a mobile application and have a wire and/or wireless connectivity to the smartphone. The mobile application has a control function controlling the ultrasound imaging unit, a storing function for storing the image generated and a display function. The ultrasound imaging unit irradiates an ultrasound wave to a part of the body and detect the reflected wave of the irradiated ultrasound. The ultrasound imaging unit may include an ultrasound irradiating member; a reflected ultrasound detection or receiving member and a control member. When the ultrasound irradiating member and the reflected ultrasound detection or receiving member are included, the control member analyzes the reflected ultrasound received and generated it as a 2D or a 3D images, which are then displayed on the screen of the smartphone and/or transmitted via a transceiver unit to a predetermined doctor or to a predetermined server of a hospital.

The control module for controlling the ultrasound imaging unit includes an ultrasound mode designation member (U') designating ultrasound imaging mode, an ultrasound amplifier amplifying the wave data of the reflected ultrasound measured by the ultrasound imaging unit, an ultrasound filtering member filtering the noise, a A/D converter converting the analog signal of the ultrasound image to a digital signal, an ultrasound signal control member detecting the ultrasound signal, and an ultrasound signal transmitting member transmitting the ultrasound signal to the smartphone and the like.

The present smartphone based telemedical device equipped with a detachable compound medical device with a thermometer and an ultrasound imaging unit may be applied or used for detecting or diagnosing or determining a pneumonia, a heart disease, a pregnancy, a liver cancer or a varicose vein and the like. It is also encompassed that the examination results obtained using the present device may be transmitted to a proper medical centers or hospitals for telemedical.

The transceiver may transmit, to the outside, the information that is read out by the controller and/or the medical data of a user which are detected by the auscultation unit or the body temperature measurement unit. For example, the transceiver may transmit the above-described data to a medical server, a medical device or an emergency disaster management server. The transceiver may transmit the body temperature data, the auscultation sounds data, the blood pressure data and/or the ultrasound image data of a user which are detected by the body temperature measurement unit and the auscultation unit to the outside, or may transmit the result of the diagnosis based on analyzing the above-described data. When the auscultation sounds data, and the ultrasound image data of a user are transmitted to the outside without transmitting the diagnosis result, the present smartphone based telemedical device does not perform a diagnosis function, but may simply perform a function of transmitting the data to an external device for diagnosis. The external device for diagnosis may include a medical server, a medical device or an emergency disaster management.

Also, the control module may include a database that stores standard data for various diseases or body temperature-heart rate correlation table for a pregnant woman for each mode; a comparing/analyzing unit searching for and comparing the detected digital data with standard data of a designated mode selected in the database; a controller storing various execution programs for controlling various units or member of the present device and for reading out or determining the name of disease, a storage unit for storing the readout information; and an output unit outputting the readout information, an LCD unit visually displaying the information or data from the output unit; an audio unit for outputting the information or data to a speaker.

In one embodiment of the present disclosure, the smartphone based telemedical device of the present disclosure determines the health status (disease diagnosis or pregnancy) of a user based on the information or data obtained by using the present device. Also such information or data may be transmitted to an external server or a device accessible by the present device, and the health status of a user may be readout from the external server or device.

The central control module of the smartphone based telemedical device of the present disclosure includes an auscultation mode designation member designating an auscultation mode; a detection member to which the auscultation microphone is connected; a filtering member filtering only the auscultation sounds detected of a designated mode and removing noise from other parts of a body not examined or noise originated from outside of a body; an auscultation signal amplifier amplifying the filtered auscultation signals; an A/D converter converting the amplified analog waveform signals into digital signals; a digital signal amplifier of the converted digital signals; a database storing standard data of various diseases according to the auscultation modes; a comparing or analyzing unit searching and comparing the detected digital data with the standard data of a designated mode that is stored in the database; a central controller controlling each units or members of the present device and diagnose or determine the name of disease; a storage unit of the readout information or data; an output unit outputting the readout information or data; a display unit visually displaying the readout information or data from the output unit; an audio unit for outputting the information or data to a speaker; a transceiver transmitting and receiving the output data or information to a medical information server, a medical device or a an emergency disaster management server; and a body temperature measurement unit connected to a temperature sensor for measuring body temperature of a user and the like.

For other processes for performing diagnosis using or based on the auscultation sounds or mode, KR Patent No: 1435581 filed May 22, 2014 and issued Aug. 28, 2014 may be referred.

Hereinafter, an algorithm for diagnosing pneumonia infection by using auscultation sounds and body temperatures in a pulmonary auscultation mode is described.

When a mode of diagnosis is a pneumonia mode, a patient may be diagnosed with pneumonia by the controller of the present device when a pneumonia diagnosis body temperature criteria and at least one of pneumonia diagnosis auscultation criteria are both satisfied.

The pneumonia diagnosis auscultation criteria include a group consisting of a pediatric pneumonia diagnosis criterion, a first pneumonia diagnosis auscultation criterion, and a second pneumonia diagnosis auscultation criterion.

The pediatric pneumonia diagnosis criterion may be applied when the patient is a child. The pediatric pneumonia diagnosis criterion may be met for 60 or more breaths per minute in children under 2 months old, 50 or more breaths per minute in children between 2 to 11 months old, or 40 times or more breaths per minute in children between 11 to 59 months old.

Also, the first pneumonia diagnosis auscultation criterion may be met when the auscultation unit detects rales, crackles, or moistrales. The moistrale refers to auscultation sounds that are similar to sounds of rubbing hair.

Also, the second pneumonia diagnosis auscultation criterion may be met when the auscultation unit fails to detects breaths during auscultation of a pulmonary area.

Also, the pneumonia diagnosis body temperature criterion may be met when the body temperature measurement unit detects fever that exceeds a predetermined range.

Reasons for setting the pneumonia diagnosis criteria as above are described below.

In medical field, the common cold (upper respiratory infection) is an acute viral rhinopharyngitis, a highly infectious disease that is caused when the upper respiratory system is infected with viruses. The disease is very common in that even adults are infected many times a year. In particular, infants and young children may be infected 6 to 8 times or more a year, and accordingly, a prevalence rate is very high. Cold may be caused by various viruses. If not severe, cold may be naturally cured by resting without taking medicines. For infants and young children, in order to alleviate symptoms of cold, the body temperature is reduced by using fever remedies such as acetaminophen or brufen.

Although the cold itself is not life threatening, pneumonia, a complication of cold, may be life threatening for children, the elderly, and the disabled, and thus requires a careful attention. Pneumonia is a main cause of the death for children of age 5 or under worldwide, and represents 13% of the infectious diseases in children of age 2 or less.

Although a thermometer is the most commonly used instrument at homes to observe symptoms of a cold patient, it is difficult to distinguish cold from pneumonia just by using the thermometer. A combination of the thermometer and a stethoscope may allow relatively more accurate determination of a pneumonia infection. For example, the World Health Organization (WHO) defines a respiratory rate for determining child pneumonia as below:

children under 2 months of age: 60 or more rapid breaths per minute children between 2 to 11 months of age: 50 or more rapid breaths per minute children between 12 to 59 months of age: 40 or more rapid breaths per minute Furthermore, pneumonia, which develops as a complication of cold, may be diagnosed at an early stage by auscultation signs such as crackles and rales.

For diagnosis of pneumonia compilations in a child with cold, body temperature measurement as well as evaluation of auscultation sounds using a stethoscope may be used as effective instruments for diagnosing pneumonia at an early stage due to cold. Typical symptoms of child pneumonia include coughs, fever, chest pain, and respiratory symptoms such as rapid breathing.

As described above, in the case of a patient suspected of pneumonia, by detecting auscultation sounds as well as local or systematic fever that occur due to infection at the same time, the rate of early pneumonia diagnosis may be increased.

Also, in the case of pneumonia caused by atelectasis, it is important to check auscultation sounds and fever. Atelectasis refers to a state in which air is absent in the lung and a portion of the lung is turned into a rubber balloon with no air inside. There are many mild cases with no symptoms, however, hypoxia, difficulty in breathing, fever and chills due to a secondary respiratory infection, and chest pain may occur. In particular, severe hypoxia and respiratory failure may lead to death.

Auscultation signs of Atelectasis include no breathing sounds heard at a certain part of a lung. When atelectasis part of the lung is affected by secondary bacterial infection and thus develops into a bacterial pneumonia, systematic both the fever due to pneumonia and the auscultation signs of pneumonia are present. Accordingly, an accurate diagnosis is possible by simultaneously acquiring a body temperature and auscultation signs.

Therefore, the present device as described above may determine whether a user has a fever due to an infection by measuring the body temperature of a user using the body temperature measurement unit of the present device. Also, by measuring the breathing pattern of a user using the auscultation unit of the present device, the user may be determined to have atelectasis symptom when there are no auscultation sound detected from the area of the lung examined.

Therefore, the present smartphone based telemedical device may determine whether a user has atelectasis lung based on the information such as fever and auscultation sound specific to atelectasis collected by the body temperature measurement unit and auscultation unit.

Also, various allergic diseases such as allergic rhinitis and asthma cannot be distinguished from common cold and pneumonia particularly in children. Thus, it is common that the time for treatment for chronic allergic diseases is missed.

Allergic diseases may generally be distinguished from cold by auscultation sounds. In particular, allergic diseases may be more accurately distinguished based on the facts that systematic fever rarely occurs in allergic diseases. Therefore, an analysis of auscultation sounds as well as regular measurement of body temperature may increase the possibility of distinguishing cold from allergic respiratory diseases such as allergic rhinitis and asthma, and thus, diagnosis and treatment may be better suited for a specific disease at an early stage.

Although chronic obstructive pulmonary disease (COPD) is a common disease that is the fourth leading cause of death according to WHO, there is no evident cure. Rapid worsening of COPD is referred to as COPD exacerbation.

This symptom gradually worsens and is a painful phenomenon that occurs at an average of 3 times a year. A typical symptom of COPD is coughs, sputum amount increase, sputum color variation, suffocating feeling in the lungs, auscultation sounds such as wheezing, and fever. The analysis of auscultation sounds and the regular measurement of body temperature variation may increase the possibility of diagnosing and curing rapid worsening of COPD at an early stage.

For example, with the present device, the controller electrically analyze the auscultation sounds detected by the auscultation unit, and determine whether wheezing is detected based on the waveforms of the sound waves measured. Also, the present device may measure the body temperature of the patient by using the body temperature measurement unit, and may diagnose rapid worsening of COPD at an early stage when fever exceeding a normal range is detected.

Hereinafter, an algorithm for diagnosing enteritis infection by using auscultation sounds and body temperatures in an enteritis auscultation mode is described.

When the mode of diagnosis is an enteritis mode, the patient may be diagnosed with enteritis by the controller of the present medical device when a first enteritis diagnosis auscultation criterion and a second enteritis diagnosis auscultation criterion are both satisfied.

The first enteritis diagnosis auscultation criterion may be met when an auscultation unit detects a metallic bowel sound. The second enteritis diagnosis auscultation criterion may be met when the auscultation unit detects a paralyzed bowel movement.

In this regard, enteritis may be divided into viral and bacterial enteritis. Enteritis that is common for children are usually viral, and the most well-known virus is pseudocholera. Symptoms include high fever, vomiting, diarrhea. However, at an early stage of infection, the symptom starts with fever. Usually 2 or 3 days of fever occurs with or without vomiting, and then, vomiting slightly decreases and diarrhea occurs.

Since early stage symptoms of enteritis are similar to those of common respiratory infection symptoms, it may be misdiagnosed resulting in the wrong treatment. Thus body temperature measurement as well as an analysis of intestinal movement auscultation sounds may allow accurate determination of enteritis at an early stage distinguishing it from respiratory diseases, leading to an effective treatment at an early stage.

Typical symptoms of rotaviral enteritis, which is most common in children, include dehydration, metallic bowel sound due to an increase in intestinal movement as detected by auscultation, and a mismatch between a heart rate and a body temperature increase rate.

Accordingly, in addition to the early stage fever, a enteritis diagnosis rate may be increased based on the abdomen auscultation sounds due to excessive intestinal movements without changes in the respiratory auscultation sounds of pneumonia. Along with a cardiac sound auscultation, a mismatch between a heart rate and a body temperature increase rate detected may increase the accuracy of the diagnosis.

Irritable bowel syndrome is a disease that involves abdominal pain, bloating, and changes in bowel habits without evident underlying disorders. Irritation bowel syndrome is a common chronic disease with a prevalence rate of 10% to 20% and an incidence rate of 1% to 2%.

For irritable bowel syndrome, an occurrence of non-specific symptoms is a warning sign indicating the need to find other underlying reasons. Progressive symptoms and systematic fever are examples of non-specific symptoms. Existence of progressive symptoms may be determined by repeating quantitative evaluation of intestinal movement according to an auscultation sound analysis performed by the auscultation unit of the present device.

Also, non-specific symptoms may be detected by performing evaluation of intestinal movement and regular measurement of body temperature variation by using the body temperature measurement unit. Systematic evaluation of intestinal movement and body temperature variation may distinguish it from an acute disease such as enteritis.

Hereinafter, an algorithm of diagnosing health status of a pregnant woman and a fetus by using auscultation sounds and body temperatures in a pregnant woman health status auscultation mode will be described.

When the mode of diagnosis is a pregnancy checkup mode, the patient may be diagnosed with a normal pregnancy by the controller of the present device when a pregnancy heart rate criterion and a pregnancy body temperature criterion are both satisfied.

The pregnancy heart rate criterion may be met when a fetal heart rate detected by the auscultation unit is within a predetermined heart rate range according to a normal fetal heart rate chart per gestational week.

The pregnancy body temperature criterion may be met when a body temperature of the patient detected by the body temperature measurement unit is within a predetermined range according to a normal basal body temperature range chart of a pregnant woman per gestational week.

In relation to this, a body temperature and a heart rate of a pregnant woman will be described in detail. The body temperature of the pregnant woman slightly decreases. It is understood that this decrease is a reaction caused by an increase in heat production because of a metabolic rate increase due to pregnancy and a direct heat production of a fetus. In average, the body temperature of the pregnant woman decreases 0.3° C. during the first 3 months and decreases 0.1° C. every month (Wang and Apgar, Am Fam Physician. 1998 Apr. 15; 57(8):1846-1852.). Thus, the pregnant woman has to exercise with caution such that a body temperature is not increased or dehydration does not occur.

The stethoscope may be used as an instrument for observing the health status of the fetus. Heart pulses of a fetus may be heard through the abdominal walls of the pregnant woman. First beating of the heart starts from the fifth gestational week, and is similar to the beating of the pregnant woman, 80 to 85 beats per minute. During the first month, the heart pulse increases everyday by 3 beats per minute. This variation is very accurate that the variation may be used instead of ultrasound examination when medically calculating the gestational week. At the ninth gestational week, the heart rate of the fetus increases to an average of 175 beats per minute. From this point, the heart rate decreases to a normal rate for a mid-phase of pregnancy, i.e., 120 to 180 beats per minute. The heart rate gradually decreases even during the last tenth week.

Although there are reports about harms of an ultrasound unit to a fetus, which is used to listen to cardiac sounds, a stethoscope is safe in that the stethoscope detects the sounds generated and thus does not affect the fetus. As described above, the pattern of decreasing in the body temperature of a pregnant woman and the pattern of generation and decreasing in the cardiac sounds of a fetus are shown to be related to each other. Therefore, when the body temperature of the pregnant woman and the cardiac sounds of the fetus are systematically linked and monitored, this can provide a great amount of assistance for an accurate diagnosis of a mother-fetus relationship and a healthy pregnancy process.

For example, the above-described device may store data about a body temperature decrease pattern of a pregnant woman per gestational week and a table of heart rates of a fetus. When the patient is a pregnant woman, the present medical device may measure a body temperature of the pregnant woman by using the body temperature measurement unit, and detect a fetal heart rate by using the auscultation unit. The controller of the device may determine a normal range of the body temperature of the pregnant woman and a normal range of cardiac sounds of the fetus based on a gestational week of the pregnant woman that is input via a user input unit. When the detected body temperature of the pregnant woman and the detected heart rate of the fetus are outside of the normal ranges, the present medical device may determine that the pregnant woman and the fetus have an abnormal health.

Also, when the present medical device is used to estimate a gestational week, a process of receiving an input of the number of pregnancy weeks via the user input unit may be omitted. The present medical device may compare a fetal heart rate detected by the auscultation unit and a body temperature of a pregnant woman detected by the body temperature measurement unit respectively with a body temperature table of a pregnant woman per gestational week and a heart rate table of a fetus per gestational week.

The compound medical device may estimate a gestational week of the pregnant woman by performing a comparison with the body temperature table of the pregnant woman and the heart rate table of the fetus.

The present device that includes a body temperature measurement unit, an auscultation unit, and a controller as described above is not limited to medical purposes.

For example, the present device that includes the above-described body temperature measurement unit, the above-described auscultation unit, and the above-described controller may be used as an educational device or a toy.

For example, when the device is used as an educational device, the device may be used as an educational supplementary instrument for teaching principles of the human body and diagnosis algorithms to an ordinary student that studies or has interest in medicine. For example, the device according to an embodiment of the present specification may be used to a patient or an educational human body model that is manufactured for educational purposes to show symptoms of a suspected disease.

Therefore, a user of the device according to an embodiment of the present invention does not have to be a doctor. A doctor, a medical student, or an ordinary user may all use the device.

Also, a patient of the device according to an embodiment of the present invention does not always have to be human, and may include a human body, a body of an animal, and an educational supplementary material for medical education.

When the device is used as a toy, children may use the device on a patient (or an educational human body model).

The above-described embodiments may be implemented as methods, apparatuses, or articles using standard programming and/or engineering techniques. The term "articles" include computer programs that may be accessed from a random computer-readable apparatus, carriers, or media. For example, computer-readable media includes, but is not limited to, magnetic memory devices (e.g., hard disks, floppy disks, and magnetic strips), optical disks (e.g., CDs, DVDs), smart cards, and flash memory devices (e.g., EEPROMs, cards, sticks, key drives). Also, various types of storage media described herein include at least one device for storing information and/or other machine-readable media.

The term "machine-readable media" includes, but is not limited to wireless channels and various types of other media which may store, hold, and/or transmit command(s) and/or data.

Descriptions of the embodiments above are provided so that one of ordinary skill in the art to which the present invention pertains may user or perform the present invention. Various changes in form and details of the embodiments will be evident to one of ordinary skill in the art to which the present invention pertains, and general principles defined herein may be applied to other embodiments without departing from the scope of the present invention. Therefore, the present invention is not limited to the embodiments provided herein, and should be interpreted in the broadest range that is consistent with the principles and novel features provided herein.

What is claimed is:

1. A telemedical device based on a smartphone comprising:
   a mobile application for medical examination installed and running on the smartphone;
   an auscultation measurement unit built into the smartphone and operated by the application;
   a body temperature measurement unit built into the smartphone and operated by the application;
   a medical image observation unit built into the smartphone and operated by the application;
   an alarm generator built into the smartphone and operated by the application; and
   a transceiver transmitting and receiving the information generated from the auscultation measurement unit, the body temperature measurement unit, the medical image observation unit and/or alarm generator to contacts predetermined through the application, wherein the auscultation measurement unit comprises a transmitting member, a noise removing member from the auscultation sound detected, a signal amplifier, a digital converter, a standard auscultation sound storing member, and a display member displaying the standard auscultation sounds compared to the standard auscultation sound, wherein the body temperature measurement unit comprises a contact or non-contact type of a temperature sensor, a body temperature storing member, and a display member displaying the temperature measured or stored, wherein the medical image observation unit comprises a camera, an observed medical image storing member and a display member displaying the medical images observed or stored, wherein the alarm generator comprises a speaker, wherein the mobile application controls the auscultation measurement unit, the body temperature measurement unit, the medical image observation unit, the transceiver and the alarm generator, and generates an alarm in emergency and transmits the alarm and/or at least one of the information generated by the auscultation measurement unit, the body temperature measurement unit and the medical image observation unit to a predetermined contact, wherein the mobile application further comprises a physical data input section for receiving at least one information selected from a group consisting of an age, a sex, a height, a body weight, a gestational week of pregnancy, and a mode of diagnosis, wherein the mode of diagnosis is selected from a pneumonia mode, enteritis mode, and a pregnancy mode, wherein the telemedical device further comprises an analyzing unit to compare and analyze the information generated in comparison to criteria for each of the mode of diagnosis stored in each of the storing members or a database to diagnose or determine a health status of a user, wherein the criteria for the pneumonia mode is a body temperature exceeding a predetermined range; and at least one of the lung auscultation sounds selected from rales, crackles or moist rales, or no lung auscultation sound;

wherein the criteria for the enteritis mode is an auscultation metallic bowel sound or no bowel auscultation sound; and wherein the criteria for the pregnancy mode is a body temperature of a pregnant woman and a fetal heart rate measured by an auscultation.

2. The telemedical device based on a smartphone of claim 1, wherein the criteria for the pneumonia further comprises a pediatric pneumonia diagnosis criteria, wherein the pediatric pneumonia criteria is a respiratory rate according to the age of a user in which the respiratory rate is 60 or more per minute for a user under 2 months old, 50 or more per minute for a user between 2 to 11 months old, 40 or more per minute for a user between 11 to 59 months old.

* * * * *